United States Patent [19]
Gardner

[11] Patent Number: 5,993,782
[45] Date of Patent: Nov. 30, 1999

[54] THERAPEUTIC METHOD FOR REVERSING HYPOSMIA IN A HUMAN PATIENT

[76] Inventor: Conrad O. Gardner, 121 Vine St. Suite 2202, Seattle, Wash. 98121

[21] Appl. No.: 09/069,490

[22] Filed: Apr. 28, 1998

[51] Int. Cl.$^6$ .................................................. A61K 9/12
[52] U.S. Cl. .............................................. 424/45; 424/46
[58] Field of Search ........................................ 424/45, 46

[56] References Cited

U.S. PATENT DOCUMENTS

| | | | |
|---|---|---|---|
| 4,335,121 | 6/1982 | Phillips et al. | 424/241 |
| 4,985,418 | 1/1991 | Richards | 514/179 |
| 5,270,305 | 12/1993 | Palmer | 514/171 |
| 5,340,572 | 8/1994 | Patel | 424/78.04 |
| 5,407,663 | 4/1995 | Eisen | 424/49 |

OTHER PUBLICATIONS

Product information publications for Flonase published by Glaxo Wellcome Inc., Research Triangle Park N.C. 22709, published Oct., 1997.

*Primary Examiner*—Raj Bawa
*Attorney, Agent, or Firm*—Conrad O. Gardner

[57] ABSTRACT

Normal olfactory function restoration through topical application of an effective amount of fluticasone propionate to the olfactory epithelium. A patient should be started on 1 mg per day dosage and the dosage gradually inreased until the patient regains the sense of smell.

1 Claim, No Drawings

THERAPEUTIC METHOD FOR REVERSING HYPOSMIA IN A HUMAN PATIENT

CROSS REFERENCES TO RELATED APPLICATIONS

Not applicable

STATEMENT REGARDING FEDERALLY SPONSORED RESEARCH OR DEVELOPMENT

Not Applicable

BACKGROUND OF THE INVENTION

1. Field of the Invention

This invention relates to a method and treatment for the reversal of hyposmia or anosmia in a human patient.

2. Description of the Related Art

PRIOR ART PATENTS AND PUBLICATIONS UTILIZING FLUTICASONE PROPIONATE FOR MEDICINAL PURPOSES

U.S. Pat. No. 4,985,418 issued to Richards Jan. 15, 1991 for the treatment of bowel disease.

U.S. Pat. No. 5,270,305 issued to Palmer Dec. 14, 1993 for respiratory disease.

U.S. Pat. No. 5,407,663 to Eisen issued Apr. 8, 1995 for mouthwash.

U.S. Pat. No. 5,340,572 to Patel et.al. Issued Aug. 23, 1994 for ophthalmic use.

U.S. Pat. No. 4,335,121 issued to Philips et.al. Jun. 15, 1982 for the treatment of inflammatory dermatoses, allergic and/or inflammatory conditions of the nose, throat, or lungs, such as asthma and rhinitis including hay fever.

Product Information publication for FLONASE, a registered trademark of Glaxo Wellcome Inc. of Research Triangle Park, N.C. 22709 comprising an aerosol formulation of fluticasone propionate, published October 1997, for the treatment of allergic rhinitis.

PRIOR ART METHOD

Smell can be adversely affected if the nasal passages are blocked by polyps or by structural abnormalities in the nasal septum or chronic sinusitis which conditions impede the passage of smells to the receptors in the olfactory epithelium, a small patch of mucous membrane lining the upper nose. Nerve fibers connected to these receptors pass through tiny holes in the bony roof of the nasal cavity to enter the olfactory bulbs routing smell information to parts of the brain.

Systemic corticosteroid therapy has been used to restore olfactory function subsequent to the failure of all other efforts to clear the air flow path including polypectomies where necessary and the use of antibiotics, antihistamines, or corticosteroids for rhinitis or allergy.

Systemic corticosteroid therapy with an oral steroid such as prednisone when successful leads most patients to accept their olfactory loss as permanent since prolonged systemic steroid use is not an option because it can lead to serious complications like diabetes or suppressed adrenal function which reduces the body's ability to respond to injury and stress.

BRIEF SUMMARY OF THE INVENTION

A method of treatment for hyposmia or anosmia comprising delivering by the intranasal route an aerosol formation of a synthetic corticosteroid in a daily dosage sufficient to cause reversal of hyposmia or asosmia and wherein said daily dosage is less than an amount causing sytemic side effects.

DETAILED DESCRIPTION OF THE INVENTION

Therepeutic Method for Reversing Steroid Dependent Asmosia

Return of sense of smell after several years loss and subsequent to polypectomies occurred in one patient over 60 years of age when only the oral steroid prednisone previously enabled successful restoration of normal olfactory function.

The hereinafter described therapeutic method for achieving restoration of the olfactory function has now been achieved without the use of systematic corticosteroid therapy and its many undesirable side effects.

Whether impairment of olfaction occurs because the olfactory cleft swells to stop air from reaching the olfactory epithelium or because inflammatory mediators alter the olfactory media and overlying mucous blanket is uncertain.

Administration of topical steroids in the form of a nasal spray such as FLONASE, a registered trademark of Glaxo Wellcome Inc. of Research Triangle Park, N.C. 22709 comprising an aerosol formulation of fluticasone propionate at normal daily doses of 200 mcg for nasal allergies did not restore olfaction. Product information of FLONASE indicates that maximum dosage for seasonal and year-round treatment of nasal allergies should not exceed 200 mcg/day and that there is no evidence that exceeding the recommended dose is more effective. U.S. Pat. No. 4,335,121 issued Jun. 15, 1992 incorporated herein by reference describes the method of manufacture of FLONASE describing therein important characteristics including the favorable ratio of topical anti-flammatory activity to undesired systemic activity of the formulated anti-inflammatory steroids of the androstane series. This important characteristic is especially highlighted in the Product Information publication for FLONASE which indicates under OVERDOSAGE that intranasal administration of 2 mg (10 times the recommended dose) of fluticasone propionate twice daily for 7 days to healthy human volunteers was well tolerated. The ability of the human patient to tolerate daily administration of 1 to 2 mg per day (5 to 10 times the recommended dose) led to the discovery of the present method for reversing hyposmia without the need for systemic corticosteroid thereby. A patient should be started on 1 mg per day dosage and the dosage gradually increased until the patient regains the sense of smell. Dosage of patients who have responded should then be reduced to a maintenance dosage sufficient to retain the patient's sense of smell thereby minimizing the possibility of systemic effects.

What is claimed is:

1. A therapeutic method for reversing hyposmia in a human patient in need thereof comprising administering to the olfactory epithelium of said patient a pharmaceutical aerosol composition comprising an effective amount of fluticasone propionate, wherein the effective amount is from 1 to 2 mg per day.

* * * * *